Jan. 7, 1964 W. FLEMER III Plant Pat. 2,337
ZELKOVA TREE
Filed Jan. 17, 1963
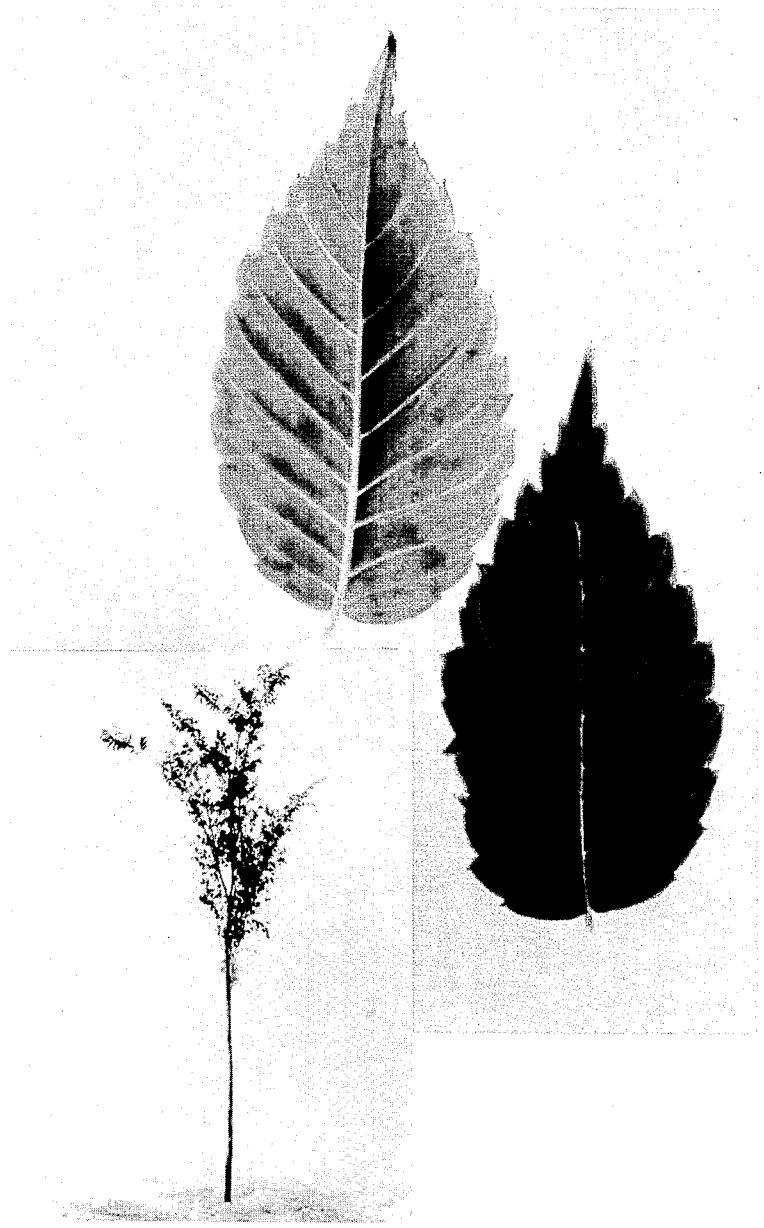
Inventor.
William Flemer III
By: Robb & Robb
Attorneys.

United States Patent Office

Plant Pat. 2,337
Patented Jan. 7, 1964

2,337
ZELKOVA TREE

William Flemer III, Princeton, N.J., assignor to Princeton Nurserymen's Research Associates, Princeton, N.J., a partnership Filed Jan. 17, 1963, Ser. No. 252,262
1 Claim. (Cl. Plt.—51)

The present invention relates to a new and distinct variety of Zelkova tree, botanically known as *"Zelkova serrata,"* which originated as a selected seedling derived from open-pollinated seedlings of the unpatented variety *"Zelkova serrata,"* identified as "Korean #55921."

At the time this new variety was selected by me, I was engaged in growing a block of open-pollinated seedlings of the *"Zelkova serrata"* variety referred to above, in the nursery of my assignee which is located in Plainsboro township, Plainsboro, New Jersey. These trees were all being grown from seed obtained from the Institute of Forest Genetics in Korea. Most Zelkova trees are crooked and ungainly in habit as young trees, but my selected seedling was of superior habit by virtue of its unusually straight and upright growth which it achieves without any special staking or corrective pruning. This improved habit has persisted through many subsequent propagations, and has convinced me that the new selected seedling represents a new and distinct variety which is different from its parents, as well as from all other Zelkova tree varieties of which I am aware, as evidenced by the following unique combination of characteristics which are outstanding therein:

(1) A rapid habit of growth;

(2) A straight and smooth trunk which occurs naturally without special staking or corrective pruning;

(3) An upright, wine-glass or vase-shaped tree head which is achieved as a young tree and which gradually spreads with age into a graceful shape corresponding to that of the American elm;

(4) Distinctive and attractive, large, thick and granular Dark Green foliage which turns to a Rusty Red color in the Fall, thus making this new Zelkova variety suitable as a replacement for American elm trees which are rapidly becoming extinct; and (5) Good insect resistance, particularly to leaf eating beetles, including the Japanese beetle, as well as to Scolytus and Hylurgopinus bark beetles.

Asexual reproduction of my new variety of Zelkova tree by budding (sometimes called bud-grafting), as performed in the State of New Jersey, shows that the foregoining characteristics and distinctions come true to form and are established and transmitted through succeeding propagations.

The accompanying drawing shows a typical young tree specimen of the new variety as depicted in black and white to illustrate its general form and habit of growth, and also shows typical specimen leaves on an enlarged scale and depicted in color to illustrate the upper and under surfaces of the foliage.

The following is a detailed description of my new variety, with color terminology in accordance with Munsell Color Chart, except where general color terms of ordinary dictionary significance are obvious:

Parentage: An open-pollinated selected seedling of an unpatented variety botanically known as *"Zelkova serrata"* (Korean #55921).

Propagation: Holds its distinguishing characteristics through succeeding propagations by budding.

Locality where grown and observed: Township of Plainsboro, Plainsboro, New Jersey.

Tree: Medium size; vigorous; with deliquescent branching habit; upright when young, but assuming a graceful wine-glass or vase-shape as it grows older; rapid growth as compared with ordinary Zelkova tree varieties.

*Trunk.*—Thick; smooth; naturally straight, which is exceptional for the species; unstaked trunks do not incline or bend over as is typical of the species.

*Branches.*—Slender; smooth-barked; wine-glass shape pattern; deliquescent; upright pattern of branches in young trees.

*Lenticels.*—Scattered; small.

Foliage:

*Leaves.*—Exceptionally large and thick for the species; turn Rusty Red color in the fall; serrate, with 10 or 11 serrations on each side of leaf, and each serration being about 1 cm. long and about .4 cm. deep; moderate, stiff, short pubescence on the veins 19 or 20 veins per leaf; alternate venation. Length (along midrib)—from 8 to 10 cm. Width —from 5.5 to 6.5 cm. Margin—coarsely serrate; upper surface: rough; granular; lower surface: granular. Color (summer color of mature leaves) —upper surface: Dull Dark Green, Plate 7.5GY3/2; under surface: Yellow Green, Plate 5.0GY5/4; veins: Yellow Green, Plate 5.0GY6/8. Petiole: very short (from about .2 to about .4 cm.); stout; covered with minute, stiff pubescence.

Flowers: None observed; flowers usually not significant in the species.

Fruit: None observed; fruit not usually significant in the species.

Insect resistance: It is not attractive to leaf eating beetles and has shown little evidence of Japanese beetle feeding when other Zelkova trees in the same vicinity were severely defoliated by beetles; also unpalatable to the Scolytus and Hylurgopinus bark beetles, as compared with other varieties grown in the same area.

I claim:

A new and distince variety of Zelkova tree, substantially as herein shown and described, characterized particularly as to novelty by the unique combination of a rapid habit of growth, a naturally straight and smooth trunk, an upright, wine-glass or vase-shaped head of branches in the young tree stage and which gradually spread into the graceful shape of the American elm as the tree grows older, distinctive, attractive, large, thick and granular Dark Green foliage which turns Rusty Red in color in the fall, and good insect resistance.

No references cited.